(12) United States Patent
Bou Aoun et al.

(10) Patent No.: US 10,668,106 B2
(45) Date of Patent: *Jun. 2, 2020

(54) CHAMBER FOR ENCAPSULATING SECRETING CELLS

(71) Applicant: Defymed, Strasbourg (FR)

(72) Inventors: Richard Bou Aoun, Strasbourg (FR); Severine Sigrist, Strasbourg (FR); Stefan Sproll, Wetzikon (CH)

(73) Assignee: DEFYMED, Strasbourg (FR)

( * ) Notice: Subject to any disclaimer, the term of this patent is extended or adjusted under 35 U.S.C. 154(b) by 15 days.

This patent is subject to a terminal disclaimer.

(21) Appl. No.: 16/031,040

(22) Filed: Jul. 10, 2018

(65) Prior Publication Data

US 2018/0311282 A1 Nov. 1, 2018

Related U.S. Application Data

(63) Continuation of application No. 15/103,108, filed as application No. PCT/EP2014/076955 on Dec. 9, 2014, now Pat. No. 10,022,404.

(30) Foreign Application Priority Data

Dec. 10, 2013 (FR) ...................... 13 62342

(51) Int. Cl.
| *A61K 35/39* | (2015.01) |
| *A61K 38/28* | (2006.01) |
| *A61K 9/00* | (2006.01) |
| *C12N 5/071* | (2010.01) |
| *A61K 9/50* | (2006.01) |
| *A61K 35/12* | (2015.01) |

(52) U.S. Cl.
CPC ............ *A61K 35/39* (2013.01); *A61K 9/0024* (2013.01); *A61K 9/5031* (2013.01); *A61K 9/5047* (2013.01); *A61K 38/28* (2013.01); *C12N 5/0677* (2013.01); *A61K 2035/128* (2013.01)

(58) Field of Classification Search
None
See application file for complete search history.

(56) References Cited

U.S. PATENT DOCUMENTS

| 4,956,219 A | 9/1990 | Legras et al. |
| 5,236,447 A | 8/1993 | Kubo et al. |
| 9,005,960 B2 | 4/2015 | Legeay et al. |
| 10,022,404 B2 * | 7/2018 | Bou Aoun ............. A61K 38/28 |

(Continued)

FOREIGN PATENT DOCUMENTS

| CH | 701975 | 4/2011 |
| DE | 195 36 033 | 4/1997 |

(Continued)

OTHER PUBLICATIONS

International Search report dated Feb. 5, 2015, in corresponding International Application PCT/EP2014/076955.

*Primary Examiner* — Aradhana Sasan
(74) *Attorney, Agent, or Firm* — Panitch Schwarze Belisario & Nadel LLP

(57) ABSTRACT

The invention relates to an encapsulating chamber for secreting cells, comprising a closed shell made of a semi-permeable membrane, said membrane comprising at least one layer of porous biocompatible polymer, and one layer of non-woven biocompatible polymer.

38 Claims, 3 Drawing Sheets

(56) References Cited

U.S. PATENT DOCUMENTS

| | | |
|---|---|---|
| 2004/0137063 A1 | 7/2004 | Legeay et al. |
| 2004/0197374 A1 | 10/2004 | Rezania et al. |
| 2006/0067917 A1 | 3/2006 | Sambanis et al. |
| 2013/0131828 A1 | 5/2013 | Legeay et al. |
| 2013/0216746 A1 | 8/2013 | Piranda |

FOREIGN PATENT DOCUMENTS

| | | |
|---|---|---|
| FR | 2 960 783 | 12/2011 |
| WO | WO 00/60051 | 10/2000 |
| WO | WO 02/060409 | 8/2002 |
| WO | WO 2008/103101 | 8/2008 |
| WO | WO 2012/010767 | 1/2012 |
| WO | WO 2012/017337 | 2/2012 |
| WO | WO 2014/173441 | 10/2014 |

\* cited by examiner

CHAMBER FOR ENCAPSULATING SECRETING CELLS

CROSS-REFERENCE TO RELATED APPLICATIONS

This application is a Continuation Application of U.S. patent application Ser. No. 15/103,108, filed on Jun. 9, 2016, now U.S. Pat. No. 10,022,404, issued on Jul. 17, 2018, which is a U.S. National Stage Application pursuant to 35 U.S.C. § 371 of International Patent Application PCT/EP2014/076955, filed on Dec. 9, 2014, and published as WO 2015/086550 on Jun. 18, 2015, which claims priority to French Patent Application 13/62342, filed on Dec. 10, 2013, all of which are incorporated herein by reference in their entireties for all purposes.

The invention relates to the field of bioartificial organs which are implantable and in particular which are in the form of chambers for encapsulating cells secreting a substance of interest. The membranes which enable such encapsulating chambers and bioartificial organs to be manufactured are also subjects of the invention.

The treatment of pathological conditions requiring a continuous supply, to the body, of substances of therapeutic interest has made necessary the development of devices which can be implanted in a patient and are capable of releasing these substances efficiently and sometimes for long periods of time.

To satisfy this need, bioartificial organs which contain cells producing one or more substances of therapeutic interest have been developed. The cells contained in a bioartificial organ are confined in internal spaces, or encapsulating chambers, delimited by at least one semi-permeable membrane. Such a membrane is termed "semi-permeable" when it allows the diffusion of the substances of therapeutic interest out of the encapsulating chamber to the target cells in the patient's body, while at the same time being impermeable to the antibodies and the cells of the patient's immune system, thus preventing them from directly attaching the cells producing the substance(s) of therapeutic interest.

A bioartificial organ is understood to be a device, in particular intended to be implanted in a patient, comprising at least one encapsulating chamber consisting of at least one semi-permeable membrane; said encapsulating chamber is intended to contain cells which secrete one or more substance(s) of therapeutic interest.

These substances of therapeutic interest are any substance intended to have a beneficial effect in the patient. These may therefore be a neurotransmitter, a hormone, a growth factor, a coagulation factor or a cytokine. In particular, these substances may be, without any limiting nature, insulin, glucagon, growth hormone, coagulation factor IX, coagulation cofactor VIII or calcitonin.

Examples of devices (bioartificial organs, semi-permeable membranes, encapsulating chambers) are known in the prior art.

Mention may thus be made of WO 02/060409 which describes a membrane consisting of a porous polycarbonate biocompatible film which is surface-modified by generation of polar sites and covered with a layer of at least one hydrophilic polymer, and the use thereof for manufacturing bioartificial organs.

WO 2012/017337 and FR 2960783 describe a functionalized semi-permeable membrane composed of a porous biocompatible support pretreated so as to increase the surface energy thereof and comprising at least two layers, each comprising a hydrophilic polymer and at least one biologically active molecule, and also the use thereof in particular for manufacturing a bioartificial organ and an encapsulation chamber.

The membrane disclosed in these documents doesn't present the two layers (porous biocompatible polymer and non-woven polymer) disclosed herein. This is clear in view of FIG. 2 of FR 2960783 which shows that the hydrophilic layers (3) have been deposited onto a unique layer of porous biocompatible polymer (2). It is also to be noted that such hydrophilic layers are envisaged in the context of the present application as described below.

WO 2012/010767 describes a bag (or pouch or pocket) for forming an implantable artificial organ, which comprises a closed shell made of a semi-permeable membrane. This bag also comprises a sheet contained in the shell, the sheet comprising projections (protuberances) on the surface thereof for maintaining a space for cells between the sheet and the shell.

US 20060067917 doesn't describe the membranes and encapsulating chamber disclosed herein. The device of D2 is different from the devices disclosed herein, in its design, and can't be confused with the encapsulation chamber of the present application, as the membranes of the device of D2 are monolayer membranes (104, 106 and 112, of FIG. 1).

WO 2000/060051 describes an encapsulation chamber, the semi-permeable membranes of which can be made from different materials and polymers (see page 21, line 15 to page 22, line 23 of this document). One should also note that WO 2000/060051 envisages the use of various materials within the macroencapsulation device, in order to maintain the cells (page 21, line 30 to page 22, line 11).

However, there is a need to make available to surgeons novel bioartificial organs which exhibit, in particular, advantageous biomechanical characteristics, i.e. good resistance after implantation. This is because bioartificial organs are intended to be implanted, generally in the intraperitoneal cavity or in the extraperitoneal space and are liable to undergo tensile or shear forces according to the movements of the recipient patient.

Moreover, these bioartificial organs must be able to contain a large number of cells, in order to be able to have a prolonged physiological effect after implantation in the patient. It is therefore necessary to design organs which are sufficiently large to do this, but they then have the drawback that they risk tearing after implantation due to the patient's movements (this problem being less significant for micro-organs containing only a limited number of cells). Increasing the thickness of the membranes in order to improve the mechanical strength cannot be a solution since the diffusion of the molecules of interest is greatly reduced when the thickness of the membrane increases.

It is therefore advisable to develop novel semi-permeable membranes with improved mechanical properties for the manufacture of bioartificial organs. The selective permeability properties must be at least retained.

In a first embodiment, the invention thus relates to a chamber for encapsulating secreting cells producing at least one substance of therapeutic interest, comprising a closed shell made of a semi-permeable membrane, delimiting a space capable of containing the secreting cells producing at least one substance of therapeutic interest, characterized in that said membrane comprises at least one layer of porous biocompatible polymer, and one layer of non-woven biocompatible polymer.

The documents cited above don't describe nor suggest such an encapsulation chamber for secreting cells, which comprises a semi-permeable membrane, which membrane comprises at least one layer of porous biocompatible polymer, and another layer of non-woven biocompatible polymer.

Furthermore, as will be seen in examples (in particular examples 7 and 8), the disclosed chambers show a higher mechanical resistance when used in a bioartificial organ, in particular after in vivo implantation.

It is recalled that the term "biocompatible" is said of a material which is well tolerated by a living organism and which does not cause a rejection reaction, a toxic reaction, a lesion or a harmful effect on the biological functions of the latter. This does not exclude the possibility of an inflammatory reaction due to the insertion of the material into the organism or of an immune reaction in the case of a biocompatible organ comprising exogenous cells; this immune reaction is not therefore due to the organ as such, but instead due to its content (secretion of chemokines by the exogenous cells).

As seen above, the semi-permeable membrane has a cut-off threshold, the molecules having a weight above this cut-off threshold being unable to cross the membrane, while the molecules having a weight below this cut-off threshold can cross the membrane. The determination of the cut-off threshold is carried out by those skilled in the art according to the characteristics of the molecules that they wish to stop or allow to penetrate.

In one preferred embodiment, and in order to allow the passing of small molecules such as insulin, glucagon or glucose and to stop the effector molecules of the immune system (such as cytokines), this cut-off threshold is between 100 kDa and 500 kDa, more preferably between 100 kDa and 150 kDa.

The internal diameter of the pores of the porous polymer makes it possible to obtain the desired cut-off threshold. Thus, in one particular case, the internal diameter of the pores present on the layer of porous biocompatible polymer is between 5 and 100 nm, entirely preferably between 5 and 50 nm.

Non-Woven Polymer

It is recalled that a non-woven polymer (non-woven) is such that the fibres thereof are maintained randomly. It is thus a sheet consisting of fibres oriented in a particular direction or randomly, bonded by friction and/or cohesion and/or adhesion. The fibres are thus arranged statistically, i.e. deposited randomly. Consequently and due to the random arrangement of the fibers, the non-woven polymer is permeable to substances, and there is no control of the size of the substances that can diffuse within the non-woven polymer.

Non-woven polymers can be produced using polymeric fibres of any type. Mention may thus be made of polyesters: PET (poly(ethylene terephthalate)), PBT (poly(butylene terephthalate)), PVC (poly(vinyl chloride)), PP (polypropylene), PE (polyethylene) or blends of these polymers.

Polyamides or polycarbonates can also be used to produce non-woven polymers.

Preferably, the non-woven polymer is chosen from polycarbonate (PC), polyester, polyethyleneimine, polypropylene (PP), poly(ethylene terephthalate) (PET), poly(vinyl chloride) (PVC), polyamide and polyethylene (PE). Blends of these polymers can also be used for producing the non-woven polymer. Poly(ethylene terephthalate) (PET) is particularly preferred.

Generally, this non-woven polymer is obtained by the meltblown method. The composition thereof is an entanglement of microfibres which have been "melt blown".

This method of production is particularly suitable for polymers which can be melt spun, in particular polypropylene, poly(ethylene terephthalate), polyamides or polyethylene.

This method generates non-wovens of greater mechanical strength.

In one particular embodiment, said membrane comprises two layers of porous biocompatible polymers, on either side of the layer of biocompatible non-woven polymer. Thus, this layer of biocompatible non-woven polymer is located, positioned or situated between these two layers of porous biocompatible polymers.

Such an embodiment makes it possible to optimize the strength of the device. Indeed, this layer of non-woven can be considered to behave like a "sponge", which gives it the capacity to absorb impacts and to deform, thus increasing the rigidity of the membrane in situ, but which can prove to be troublesome in the presence of cells, which can have a tendency to form aggregates around this non-woven. Locating the layer of non-woven between two porous layers of biocompatible polymers thus makes it possible to prevent the aggregation of cells while at the same time providing the device with additional protection/strength, and with no effect on the molecular diffusion of the biological substances.

It is not necessary for the porous and non-woven biopolymers to be identical.

Likewise, in the presence of two layers of porous biopolymers, the latter can be the same polymer or different polymers.

Porous Biocompatible Polymer

The porous biocompatible polymer consists of a polymer known in the art. Thus, it may be chosen from polycarbonate (PC), polyester, polyethyleneimine, polypropylene (PP), poly(ethylene terephthalate) (PET), poly(vinyl chloride) (PVC), polyamide and polyethylene (PE).

In one particular embodiment, at least one layer or the two layers, as appropriate, is (are) made of poly(ethylene terephthalate) (PET).

The pore formation is carried out by any method known in the art. In particular, it is possible to use the electron bombardment method or the heavy ion bombardment method (this second technique is in particular described in patent U.S. Pat. No. 4,956,219). In the case of heavy ion bombardment, the density of the heavy ions bombarded at the surface of the biocompatible support determines the pore density, while the chemical erosion treatment time determines the pore size.

The membranes are thus prepared using the "track-etching" process known in the prior art and described in particular in patents U.S. Pat. No. 4,956,219, DE19536033 or CH701975.

This technology consists in irradiating a polymer film by means of energetic heavy ions, resulting in the formation of linear latent traces characterized by a local degradation of this polymer; these traces are then revealed in the form of pores by means of a selective chemical attack.

The membrane is irradiated with a beam of heavy ions. The heavy ions pass through the entire thickness of the polymer film. In passing through the polymer, the heavy ions destroy or cut the polymer chains and thus form a clean straight opening through the material. The final alignment of the pores is determined by the angle of the beam relative to the polymer film during the irradiation process. The beam may thus be perpendicular to the polymer film or at any other angle.

In the next step, the film is passed through a bath of a strong acid such as nitric acid and the openings become pores after contact with alkaline solutions such as sodium hydroxide or potassium hydroxide.

Contrary to the rest of the film, these openings made by the ions allow the alkaline solution to pass through, said alkaline solution filling them and allowing the etching of the pores by removing the material (polymer) around these openings.

The pore size is controlled by the concentration of the alkaline solution, the contact time and the temperature of the solution.

If polyester or polycarbonate is used, the membrane obtained is hydrophilic and can either be used as it is or else be treated using surface treatment processes (plasma, spraying or coating).

The preparation of membranes according to this "track etching" technology is more precisely described in patents U.S. Pat. No. 4,956,219 and CH701975.

This technology enables the production of porous polymer membranes characterized in particular by a flat surface and a narrow cut-off threshold.

The advantage of using membranes obtained by this technology is the great accuracy of the pore size, of the number of pores, and of the shape of the pores.

The pores are preferentially cylindrical, but this technology can also make it possible to obtain pores of other shape, such as of conical shape.

Preferentially, the pores are aligned, and have an angle of between 10° and 45°, relative to the vertical, but can also have angles>45° or <10°. These angles are obtained according to the angler of the beam of ions during the bombardment of the membrane.

This technology is applicable to various materials, such as polycarbonate (PC), polyester (PET) or polyimide (PI). Polyamide, poly(vinylidene fluoride), polyacrylate or polyolefins can also be used.

This method makes it possible to easily obtain pores with a controlled size of between 0.02 µm and 15 µm, a pore density of between $10^3$ pores/cm$^2$ and $10^{10}$ pores/cm$^2$ and membranes with a thickness of between 5 µm and 80 µm.

It is to be noted that, without the treatment to form pores on the biocompatible polymer, such polymer would remain impervious to any substance, and would not allow diffusion of the substance of interest from the inner part of the biocompatible organ to the outer part. The pores only allow the diffusion of substances that are below the cutoff (i.e. that are smaller than the pore diameter).

It is thus clear that the layer of the non-woven biocompatible polymer and layer of the porous biocompatible polymer are different layers, made of different materials, and presenting different properties (in particular with regards to the passing and diffusion of substances through each layer).

In one preferred embodiment, at least one of the layers of porous biocompatible polymer of the membrane is made hydrophilic. The hydrophilicity property can be achieved by generating polar sites at the surface of this layer of porous biocompatible polymer. This surface modification can be carried out by physical means (such as the generating of charged polar sites at the surface, in particular by plasma surface treatment, by corona discharge or by electromagnetic discharge at atmospheric pressure or under vacuum) or chemical means (an alkaline treatment, in particular with sodium hydroxide, can be envisaged).

Preferentially, the layer of porous biocompatible polymer is treated with a radiofrequency argon, hydrogen, oxygen or air plasma. It can be treated at a plasma reactor emission power of between 3 and 10 watts per litre of reactor capacity, for between approximately 1 and 20 minutes. The treatment can also be carried out using a microwave plasma, at the same power, but for 5 seconds to 20 minutes. Preferably, the plasma treatment is carried out under vacuum.

Patent applications WO 02/060409 and WO 2012/017337 describe in particular the plasma surface treatment for introducing polar sites onto the porous biocompatible polymer.

After at least one layer of porous biocompatible biopolymer has been made hydrophilic, it is possible to cover it with at least one layer of hydrophilic polymer, or even with two layers of different hydrophilic polymers. An active molecule can optionally be contained in at least one layer of hydrophilic polymer.

WO 02/060409 and WO 2012/017337 also describe the addition of at least one hydrophilic polymer on the surface of a porous biocompatible polymer, said surface having been treated to make it hydrophilic, in particular by adding polar sites.

Hydrophilic Polymer

For the purposes of the invention, what constitutes a hydrophilic polymer is a polymer or a blend of polymers, which, after application on a film of porous biocompatible polymer, has an angle value of less than 40°, preferably less than 30°, after measurement according to the "sessile drop" test described in Example 2 of WO 02/060409.

It should be noted that the angle value according to the "sessile drop" test can vary depending on the treatment of the polymer. Thus, contact angles of less than 20° (of about 16-17°) can be observed for the biocompatible biopolymer, when two plasma treatments are carried out, this angle increasing (generally less than 30°) when the hydrophilic polymer (in particular HPMC) is deposited after the two plasma treatments. If a blend of hydrophilic polymers, which also contains a molecule with biological activity (in particular an HPMC, ethylcellulose+heparin mixture), is used, the angle may be greater than 30°, but remains less than 40°.

Preferentially, the hydrophilic polymer is soluble in water. This is because, due to of the implantation of the bioartificial organ in the body of a host organism, use of organic solvents is excluded since their complete elimination is difficult, and their presence, even in small amounts, is not compatible with a therapeutic or surgical use in humans or animals.

Preferably, the hydrophilic polymer material is chosen from the following hydrophilic polymers:
- celluloses and derivatives thereof, such as ethylcellulose (EC), hydroxypropylmethylcellulose (HPMC) or carboxymethylcellulose (CMC);
- polyacrylamides and copolymers thereof;
- polyvinylpyrrolidone (PVP) and copolymers thereof;
- polyvinyl alcohols;
- vinyl acetate copolymers, such as a poly(vinyl acetate)/poly(vinyl alcohol) copolymer;
- polyethylene glycols;
- propylene glycols;
- hydrophilic poly(meth)acrylates;
- polysaccharides;
- chitosans.

As hydrophilic polymer, use is made of both a polymer material consisting of one of the hydrophilic polymers as defined above and a blend of several of the hydrophilic polymers above, generally a blend of two or three of the hydrophilic polymers above.

Preferably, the hydrophilic polymer is chosen from cellulose-based compounds, in particular HPMC, EC, TEC or CMC, polyvinylpyrrolidones, poly(vinyl alcohol)s, or polyacrylates such as poly(hydroxyethyl acrylate) (HEA) or acrylic acid copolymers.

The hydrophilic polymer may also be composed of a blend of two or more hydrophilic polymers mentioned above, in particular a blend of HPMC and CMC, or of HPMC and EC.

Celluloses and cellulose derivatives, in particular hydroxypropylmethylcellulose (HPMC), are preferred.

Membrane Lamination

For greater mechanical stability, the porous biocompatible polymer membrane is reinforced using a membrane made of non-woven.

The combining of a non-woven polymer and of the porous membrane of biocompatible polymer is preferentially carried out by lamination, using methods known in the art, such as thermal lamination, with or without the presence of adhesives, preferably without adhesive.

Thus, the reinforcement of the membrane can be improved via a multilayer system alternating layers of woven or non-woven polymers and of biocompatible porous polymers. However, any degradation of the diffusion properties should be avoided.

In particular, the mechanical stability can be increased by combining a thin functional membrane which has a high pore density with a thick protective membrane which has a low pore density.

There is no limitation to the number of layers of polymers that can be used to manufacture the membrane.

Active Molecule

As indicated above, the hydrophilic polymer deposited on the layer of porous biocompatible polymer can optionally contain an active molecule.

This "active molecule" is mixed with the hydrophilic polymer. It is intended to be released into the medium surrounding the semi-permeable membrane in particular in order to reduce the inflammation due to the implantation of the bioartificial organ, and/or to induce a positive response (in particular increased vascularization) by the tissue(s) of the patient receiving the bioartificial organ.

Thus, the active molecule is chosen from anti-inflammatory agents, anti-infective agents, anaesthetics, growth factors, agents which stimulate angiogenesis and/or which induce vascularization, agents which induce healing, immunosuppressive agents, antithrombotics including antiaggregants and anticoagulants, angiotensin-converting enzyme (ACE) inhibitors, or any molecule which stimulates insulin secretion (IGF, glucagon-like peptide 1 (GLP-1) or its derivatives, incretin mimetics).

Among the anti-inflammatory agents, mention may be made of non-steroidal anti-inflammatories (NSAIDs), such as acetaminophen, aminosalicylic acid, aspirin, celecoxib, choline magnesium trisalicylate, declofenac, diflunisal, etodolac, flurbiprofen, ibuprofen, indomethacin, interleukin IL-10, IL-6 mutein, anti-IL-6, NO synthase inhibitors (for example, L-NAME or L-NMDA), interferon, ketoprofen, ketorolac, leflunomide, mefenamic acid, mycophenolic acid, mizoribine, nabumetone, naproxen, oxaprozin, pyroxicam, rofecoxib, salsalate, sulindac and tolmetin, and corticoids such as cortisone, hydrocortisone, methylprednisolone, prednisone, prednisolone, betamethasone, betamethasone dipropionate, betamethasone valerate, beclomethasone dipropionate, budesonide, dexamethasone sodium phosphate, flunisolide, fluticasone propionate, paclitaxel, tacrolimus, tranilast, triamcinolone acetonide, fluocinolone acetonide, fluocinonide, desonide, desoximetasone, fluocinolone, triamcinolone, clobetasol propionate and dexamethasone. Ibuprofen is particularly suitable and preferred.

Use is preferably made of antithrombotics such as antiaggregants (acetylsalicylic acid, clopidogrel, ticlopidine, dipyridamole, abciximab, eptifibatide and tirofiban), anticoagulants (heparin, bivalirudin, dabigatran, lepirudin, fondaparinux, rivaroxaban, epoprostenol, warfarin, phenprocoumon, protein C, drotrecogin alfa, antithrombin, pentosan) and thrombolytics (alteplase, urokinase, tenecteplase and reteplase).

The use of a heparin is particularly preferred.

In another embodiment, ibuprofen is used.

In addition, it is possible to use a molecule which makes it possible to induce vascularization of the tissues surrounding the bioartificial organ, in particular PDGF (platelet derived growth factor), BMP (bone morphogenetic protein), VEGF (vascular endothelial growth factor), VPF (vascular permeability factor), EGF (epidermal growth factor), TGF (transforming growth factor) and FGF (fibroblast growth factor).

It is also possible to use IGF-1 and IGF-2, a neurotrophic factor (NGF).

In one particular embodiment, a cell growth factor is chosen which promotes vascularization by inducing angiogenesis, such as basic fibroblast growth factor (bFGF), vascular endothelial growth factor (VEGF), platelet derived endothelial cell growth factor (PDGF A or B), bone morphogenetic protein (BMP 2 or 4), or hepatocyte growth factor (HGF).

For the preparation of the layer of hydrophilic polymer and biologically active molecule, the hydrophilic polymer or the blend of hydrophilic polymers is dissolved in water.

The addition of the hydrophilic polymer optionally containing an active molecule to the layer of porous biocompatible polymer is carried out according to the methods described in WO 02/060409 and WO 2012/017337.

In another embodiment, it is possible to add, at the surface of the porous biocompatible polymer, two layers each comprising a hydrophilic polymer and at least one biologically active molecule, as described in WO 2012/017337.

Physical Characteristics of the Biocompatible Membrane

In the preferred embodiment, the membrane according to the invention comprises two layers of porous biocompatible polymer, each covered with at least one hydrophilic polymer, which surround the layer of non-woven.

Pore Diameter and Density

As seen above, the pores are introduced into each of the layers of porous biocompatible polymer using methods known in the art. It is preferred for at least the layer (if it is the only one) or one of the two layers of porous biocompatible polymers to have a pore density greater than $10^6$ pores/cm$^2$, preferably greater than $10^7$ pores/cm$^2$. This pore density is generally less than $10^{11}$ pores/cm$^2$, preferably less than $10^{10}$ pores/cm$^2$. Use is therefore made of membranes which can have a pore density preferentially greater than $10^6$ pores/cm$^2$, more preferably greater than $10^7$ pores/cm$^2$. This density is preferentially less than $10^{11}$ pores/cm$^2$, or even less than $10^{10}$ pores/cm$^2$. This density is therefore between $10^6$ pores/cm$^2$ and $10^{11}$ pores/cm$^2$. A density greater than $10^9$ and less than $10^{10}$ pores/cm$^2$ is perfectly suitable.

As seen above, the pores of the layers of porous biocompatible polymer have an internal diameter such that they allow semi-permeability of the membrane.

Thus, at least one of the two layers (or the only layer if such is the case) of porous biocompatible polymer has pores which have an internal diameter greater than 5 and preferably greater than 10 nm, and less than 100 nm, and preferably greater than 10 nm and less than 50 nm, more preferably less than 40 nm. A pore diameter of less than 90 nm is also very favorable for this layer of porous biocompatible polymer, as such pore diameter maintains the semi-permeability property, that is sought for the membrane. The pore density is then advantageously greater than $2.10^9$ and less than $4.10^{10}$ pores/cm$^2$.

When the membrane has two layers of porous biocompatible polymers, the internal diameter of the pores of one of the layers is preferentially as above.

The internal diameter of the pores of the second layer may be larger, the cut-off effect at the desired size being given by the diameter of the pores of the first layer. Thus, the internal diameter of the pores of the second layer may be greater than 100 and less than 2000 nm, preferably greater than 200 nm. These pores preferably have an internal diameter less than 1000 nm. An internal pore diameter greater than 400 and less than 600 nm, or of approximately 500 nm, is perfectly suitable. The pore density is then advantageously greater than $5.10^6$ and less than $5.10^7$ pores/cm$^2$.

When the membrane comprises two layers of porous biocompatible polymer, which surround the layer of non-woven, it is preferable for the encapsulating chamber to be such that the layer for which the pore diameter is the smallest is situated inside the chamber (in contact with the secreting cells producing at least one substance of therapeutic interest) and that the layer for which the pore diameter is the widest is situated on the outside (in contact with the patient's body).

Membrane Thickness

In one preferred embodiment, the total thickness of the membrane (comprising the layer of non-woven polymer and the layer(s) of porous polymer(s)) is greater than 45 µm. It is generally, and preferably, less than 200 µm, but can also be greater than this size; thicknesses ranging up to 300 µm, or even beyond, can in particular be envisaged. Preferably, it is greater than 50 µm. It is also preferentially less than 150 µm. This membrane thus generally has a thickness of between 45 and 200 µm.

When the membrane has two layers of porous biocompatible polymers, said layers can have the same thickness or have different thicknesses.

The layer of non-woven polymer generally has a thickness greater than 40 µm, preferably greater than 60 µm, more preferably greater than 80 µm. This layer has a thickness generally less than 250 µm and preferably less than 150 µm. Thus, the thickness of the layer of non-woven polymer is often between 40 µm and 150 µm.

When the membrane has only one layer of biocompatible polymer, said layer then has a thickness greater than 5 µm. This layer is less than 200 µm, preferably less than 100 µm, being, however, preferably less than 50 µm.

When the membrane has two layers of porous biocompatible polymer, and said layers have different thicknesses, the thickness of the first layer is then greater than 5 µm. It is also preferably less than 200 µm, but preferably less than 40 µm; a thickness less than 15 µm (and preferably greater than 5 µm) is perfectly suitable. This thickness is preferentially the thickness of the layer which has pores with the smallest internal diameter, if the internal pore diameter is different for the two layers.

The thickness of the second layer is generally greater than 25 µm. It is preferably less than 200 µm, preferably less than 100 µm, more preferably less than 50 µm; a thickness of between 30 and 50 µm is perfectly suitable.

The thickness of each layer of hydrophilic polymer optionally present on one or the two layer(s) of porous biocompatible polymers is negligible, compared with the total thickness of the membrane. It is in fact preferably less than 500 nm and generally between 25 and 250 nm.

In one preferred embodiment, the membrane has two layers of porous biocompatible polymers on either side of a layer of non-woven polymer.

In this embodiment, one layer of porous biocompatible polymer has pores with an internal diameter greater than 100 nm, preferably greater than 200 nm, more preferably greater than 400 and less than 1000 nm, more preferably less than 600 nm, preferably at a density of about $5.10^7$ pores/cm$^2$. It is then advantageous for this layer to be the one with a thickness of between 25 and 200 µm (see above).

The other layer of porous biocompatible polymer has pores with an internal diameter greater than 5 nm, preferably greater than 10 nm (and generally less than 100 nm, preferably less than 50 nm, preferably less than 40 nm), preferably at a density of about greater than $2.10^9$ pores/cm$^2$. This density is also preferentially less than $7.10^9$ pores/cm$^2$.

It is advantageous for this to be the layer with a thickness of between 5 and 200 µm (preferably 5 to 15 µm).

Encapsulation Chamber

The invention also relates to a chamber for encapsulating secreting cells producing at least one substance of therapeutic interest, comprising a closed shell made of a membrane according to the invention, delimiting a space capable of containing the secreting cells producing at least one substance of therapeutic interest. This encapsulating chamber can also be referred to as a "pouch" and makes it possible to form a bioartificial organ which is implantable in the patient.

In one particular embodiment, this encapsulating chamber also comprises a biocompatible sheet contained in said shell, said sheet preferably comprising projections (also designated as protuberances) at its surface. These projections are advantageous for maintaining a space for the cells between the sheet and the shell, but also for distributing the cells in a homogeneous and planar manner, thus making it possible to maximize the exchange surface. This sheet is preferentially made of silicone.

Such an embodiment is described in application WO 2012/010767. Thus, in one preferred embodiment, the shell is formed from two membranes which are heat-welded together. Use may be made of the method described in WO 2012/010767 or a method of heat-welding using ultrasound, known in the art. The method for forming the shell is simple and makes it possible to enclose the sheet in the shell.

Shape of the Chamber

In one preferred embodiment, the encapsulating chamber is circular. Such a shape has several advantages:
- absence of "corners" or protruding parts which are capable of creating cell or inflammatory aggregates during the implantation,
- ease of manufacture of the encapsulating chamber (no need to orient the two membranes and the sheet before the heat-welding).

In one particular embodiment, the diameter of the encapsulating chamber is greater than 3 cm, preferably greater than 5 cm, or than 8 cm. It is generally less than 20 cm, and is preferentially less than 15 cm, or than 14 cm. A diameter of between 8 and 14 cm is perfectly acceptable.

When the chamber is not round, the largest dimension thereof is generally greater than 3 cm, preferably greater than 5 cm, or than 8 cm. It is generally less than 20 cm, and is preferentially less than 15 cm, or than 14 cm.

Volume of the Chamber

As seen above, the encapsulating chamber preferentially makes it possible to manufacture a "macro" organ when the secreting cells producing at least one substance of therapeutic interest are introduced therein, i.e. it allows said cells to secrete this substance for a considerable period of time (greater than 3 months, preferentially greater than 6 months) at levels which are of physiological interest (i.e. making it possible to meet the patient's need). The encapsulating chamber should therefore be able to receive a large number of cells.

It is generally estimated that the preferred internal volume of the encapsulating chamber should be greater than 15 ml, preferably greater than 20 ml, more preferably greater than 25 ml, and can rise to 50 ml, for use in humans. For use in other animals, the volume will be different (approximately 1 ml in rats, for example).

Such encapsulating chambers must be able to contain a large number of cells. In the context of the treatment of diabetes, it must be possible to encapsulate the equivalent of at least 500 000 islets of Langerhans, preferably the equivalent of more than 700 000 islets, and optionally up to the equivalent of one million islets of Langerhans. In the knowledge that one islet contains, on average, about 1000 cells, this gives an estimation of the number of cells that the encapsulating chamber according to the invention can contain.

The number of cells will obviously vary according to the type of cells that it is desired to encapsulate and implant in the patient.

In one preferred embodiment, the membrane forming the encapsulating chamber comprises two layers of porous biocompatible polymers on either side of the non-woven polymer. In this embodiment, it is preferred for at least the internal layer (situated inside the chamber after formation of the chamber) to be the layer on which the pores provide the semi-permeable nature of the membrane (cut-off threshold), i.e. which has the pores that have an internal diameter greater than 5 nm (and generally less than 100 nm) or having the other dimensions mentioned above.

The layer external to the shell (in contact with the patient's tissues and cells) can have pores with a larger internal diameter, in particular greater than 100 nm, but preferably less than 2000 nm, or having the other dimensions mentioned above.

In one embodiment, and as described in WO 2012/010767, the encapsulating chamber can comprise at least one connector (in particular attached to the shell and/or the sheet), which makes it possible to establish a communication between the exterior and the interior of the shell. Connecting these connectors to flexible tubes makes it possible to fill and empty the chamber.

Bioartificial Organ

The invention thus relates to a bioartificial organ comprising at least one encapsulating chamber according to the invention. Such a bioartificial organ also advantageously presents the tubes connected to the connectors and making it possible to fill and empty the bioartificial organ, making it possible to renew the content of the bioartificial organ when it is implanted in a patient, without performing an explanation.

This bioartificial organ may contain various cell types.

Cells Encapsulated in the Bioartificial Organ

The cells present in the bioartificial organ produce at least one biologically active substance of interest. They can in particular be insulin-secreting cells or islets of Langerhans, which produce insulin, when the encapsulating chamber is intended for the manufacture of a bioartificial pancreas.

The cells may also be hepatic cells when the encapsulating chamber is intended for the manufacture of a bioartificial liver.

In one particular embodiment, the cells are transfected or transformed with at least one nucleic acid allowing the expression of a biologically active substance of interest. Among the biologically active substances of interest, mention may be made, by way of illustration, of insulin, cytokines, peptide hormones, growth hormone, coagulation factors VIII and IX and calcitonin.

Generally, the term "biologically active substance" is intended to mean a substance which is released or secreted by the cell which produces it and which exerts its effect on a target cell or a target molecule in the host organism, for instance a neurotransmitter, a hormone, a growth factor, a coagulation factor or a cytokine.

A great diversity of cells can be used, including immortalized cell lines, for instance primary cultures of dividing cells, or else pluripotent stem cells.

The cells can, for example, be myoblasts, which are cells that are precursors of muscle cells derived from the stem cell populations of the mesoderm, and which can be easily transformed with a nucleic acid allowing the expression of the biologically active substance of interest. Those skilled in the art may advantageously refer, for example, to WO 94/02129, WO 93/03768 or WO 90/15863.

Preferably, the cells contained in an encapsulating chamber according to the invention are embedded in a matrix, such as a matrix of collagen type IV or of fibrin, where appropriate in combination with laminin, entactin and heparan sulphate.

The cells contained in an encapsulating chamber according to the invention can generally be embedded in a matrix composed of any product or combination of products allowing the immobilization of these cells in a viable form.

The cells producing at least one biologically active substance of interest can also be encapsulated in an alginate matrix.

Manufacture of an Encapsulating Chamber

The encapsulating chamber is manufactured by any method known in the art.

Use is preferably made of the teaching of WO 2012/010767, which should be considered to be an integral part of the present application.

The invention thus relates to a method for manufacturing an encapsulating chamber according to the invention, comprising a step of heat-welding two membranes according to the invention (or even a folded membrane), in such a way as to form a pouch intended to receive cells producing at least one biologically active substance of interest.

In one particular embodiment, as seen above, the encapsulating chamber contains a sheet, and also one or more connectors. The method for manufacturing such a pouch is described in WO 2012/010767. The reader is invited to refer to WO 2012/010767 for more detailed explanations regarding the process for manufacturing the encapsulating chamber.

EXAMPLES

Example 1: Manufacture of Semi-Permeable Membranes

Figure 1:
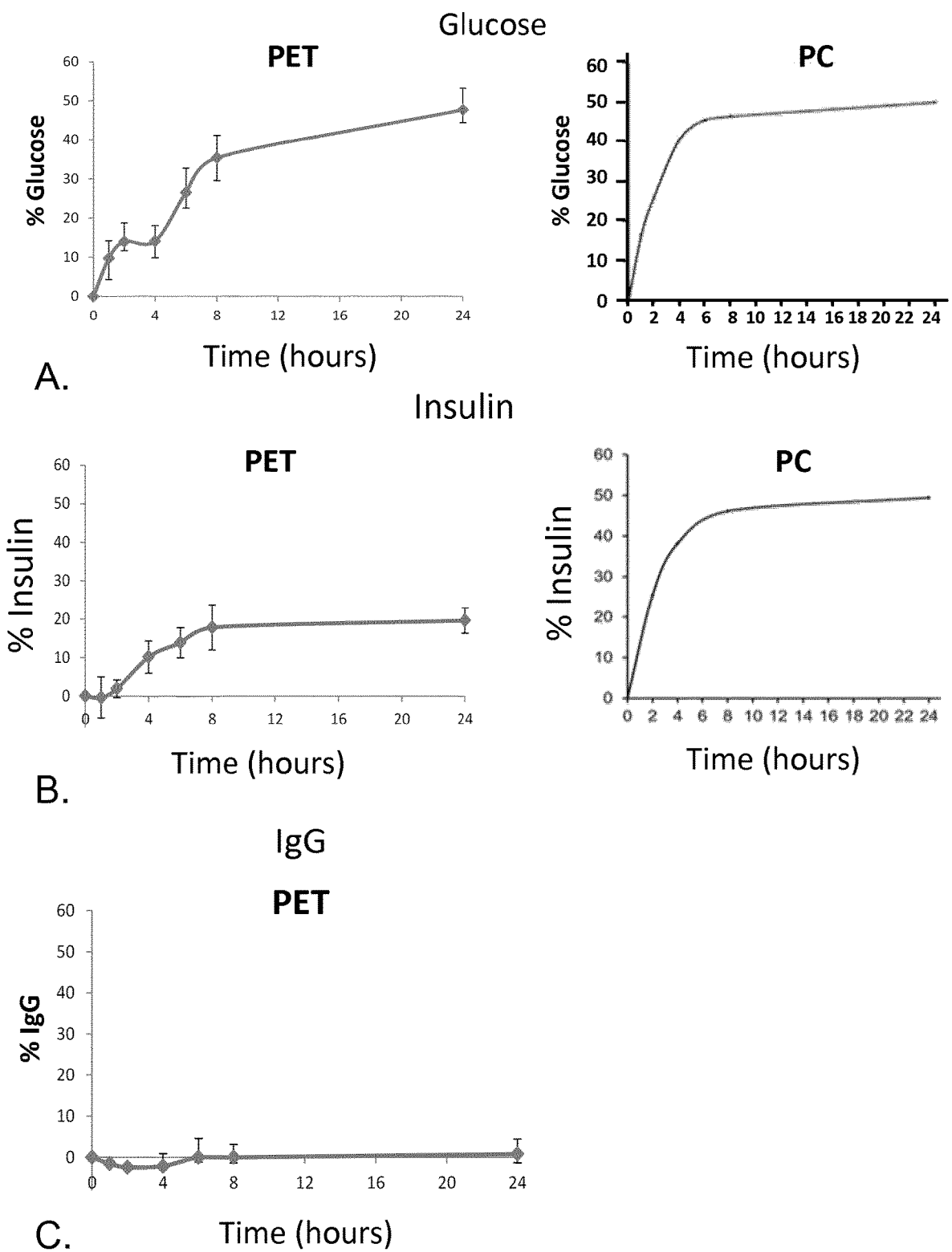
FIG. 1: Permeability of poly(ethylene terephthalate) (PET) or polycarbonate (PC) membranes according to the invention, treated or not treated with heparin, ethylcellulose (EC) and hydroxypropylmethylcellulose (HPMC), to glucose (A), insulin (B) and IgGs (C) under static conditions.
Figure 2:
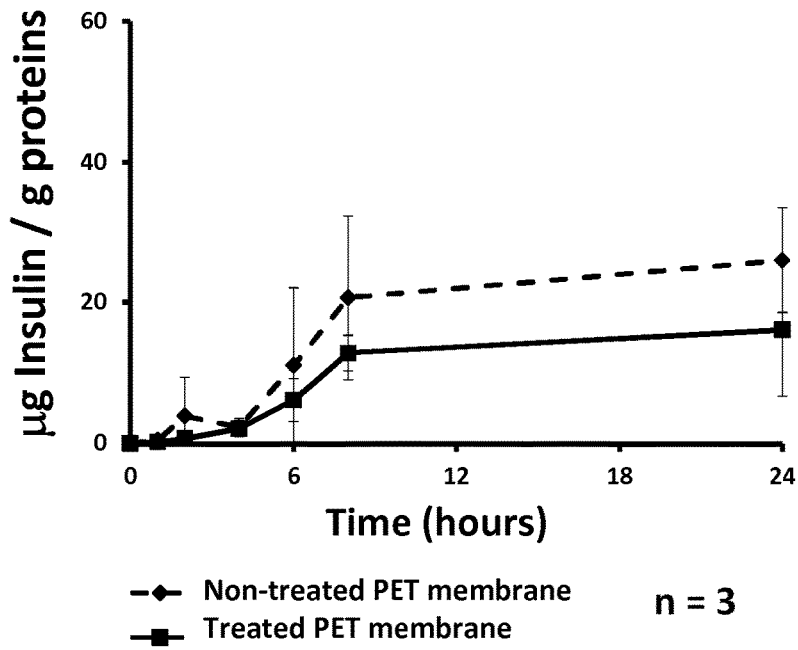
FIG. 2: Insulin secretion by rat pancreatic islets stimulated with glucose through a PET membrane according to the invention, treated or not treated with heparin, EC and HPMC. A beginning of diffusion of the insulin starting from 4 hours and a permeability which appears to be improved at 24 hours by the surface treatment are observed.

The membranes are manufactured such that two porous PET (poly(ethylene terephthalate)) layers were prepared from biocompatible PET films by the "track-etching" process, followed by lamination with the layer of non-woven PET having a density between 30 and 60 g/m2 (situated between the two porous biocompatible PET layers). A thermal lamination is carried out without the use of adhesives. One of the porous PET layers has a pore density between $2 \cdot 10^9$ and $7 \cdot 10^9$ pores/cm$^2$ with an internal pore diameter between 10 and 30 nm. The thickness of this membrane is between 8 and 12 µm. The other porous PET layer has a pore density between $10^7$ and $5 \cdot 10^7$ pores/cm$^2$ with an internal pore diameter between 400 and 600 nm. The thickness of this membrane is between 30 and 50 µm. The total thickness of the membrane is less than 200 µm.

Example 2: Surface Treatment of the Membranes

The membranes prepared according to Example 1 were subjected to a surface treatment according to the protocol of Example 1 of WO 2012/017337.

The membranes are functionalized with a first layer of heparin mixed with a solution of ethylcellulose (EC), then covered with a layer of hydroxypropylmethyl-cellulose (HPMC).

Example 3: Characterization of the Membrane Permeability

Tests for glucose-permeability, insulin-permeability and immunoglobulin (IgG)-permeability of the previously prepared membranes were carried out according to the following protocol:
Material
Diffusion chamber consisting of a top compartment and a bottom compartment separated by the membrane, the permeability of which it is desired to test (the leaktightness between the two compartments is provided by a seal), glucose (Fischer Scientific, Illkirch, France, ref: G/0500/53), NaCl, IgG (Sigma, Lyon, France, ref: 19640), insulin (Sigma, ref: 19278), distilled water.

Preparation of Solutions
Physiological saline
For 1 l: 9 g of NaCl are dissolved in 1 l of distilled water.
Glucose (4 g/l)
For 1 l: 4 g of glucose are dissolved in 1 l of physiological saline.
IgG (5.75 µg/ml)
For 60 ml: 34.5 µl of stock solution of IgG (10 mg/ml) are diluted in 59.966 ml of physiological saline.
Insulin (100 µg/ml)
For 60 ml: 60 µl of stock solution of insulin (10 mg/ml) are diluted in 59.960 ml of physiological saline.
Protocol
3 ml of physiological saline are introduced into the bottom compartment of the diffusion chamber, and the membrane, the permeability of which it is desired to test, is placed on the physiological saline while avoiding the presence of air bubbles. 3 ml of glucose solution are introduced into the top compartment, then the diffusion chamber is closed with parafilm and is incubated at 37° C.

At the end of the incubation time, 1 ml of the solution contained in the top compartment of the diffusion chamber is removed after gentle homogenization. The membrane is then removed and 1 ml of the solution of the bottom compartment is removed after homogenization.

Enzymatic assaying of the glucose is carried out using the Glucose RTU® kit (BioMérieux, Craponne, France ref: 61 269). The insulin and the IgGs are assayed using the bicinchonic acid (BCA) method by means of the Quantipro BCA Assay kit (Sigma, ref: QPBCA-1KT). The results are expressed as percentage permeability, calculated in the following way:

$$\text{Permeability(as \%)} = (C_{bottom\ compartment} / C_{top\ compartment} + C_{bottom\ compartment}) \times 100$$

C: concentration of glucose, IgG or insulin.

At equilibrium, the concentrations in the top compartment and in the bottom compartment are identical, which corresponds to a maximum permeability of 50%.
Results The results are shown in FIG. 1. Multilayer poly(ethylene terephthalate) (PET) membranes according to the invention (Example 1), and also prior art membranes as described in WO 02/060409 or WO 2012/017337, made of polycarbonate and having a layer of heparin mixed with EC and a layer of HPMC, were tested.

A slower diffusion of insulin and of glucose was observed with the PET membranes. Without wishing to be bound by this theory, it is possible that this is due to the presence of the multilayers of which they are composed.

The PET membranes are totally impermeable to IgGs.

Example 4: Semi-Permeable Membrane Implantation Tests

The membranes are implanted in the peritoneal cavity of healthy Wistar rats, according to the protocol described in Example 3 of WO 2012/017337.

The protocol relating to the taking of the samples was however modified and the samples are taken in the following way:
Taking Tissue Samples
Solutions Used
2.5% glutaraldehyde prepared, under a hood, from 25% glutaraldehyde (Sigma, ref: G5882—10×10 ml) diluted to ten-fold in ultrapure water.
PBS (reference: Gibco—14190-094).

Pot prefilled with 4% paraformaldehyde (Labonord, ref: PFFOR0060AF59001).

The membranes tested are the PET membranes according to the invention (multilayer) and the PC membranes of the prior art, optionally having undergone a surface treatment in order to deposit heparin, EC and HPMC.

Figure 3:
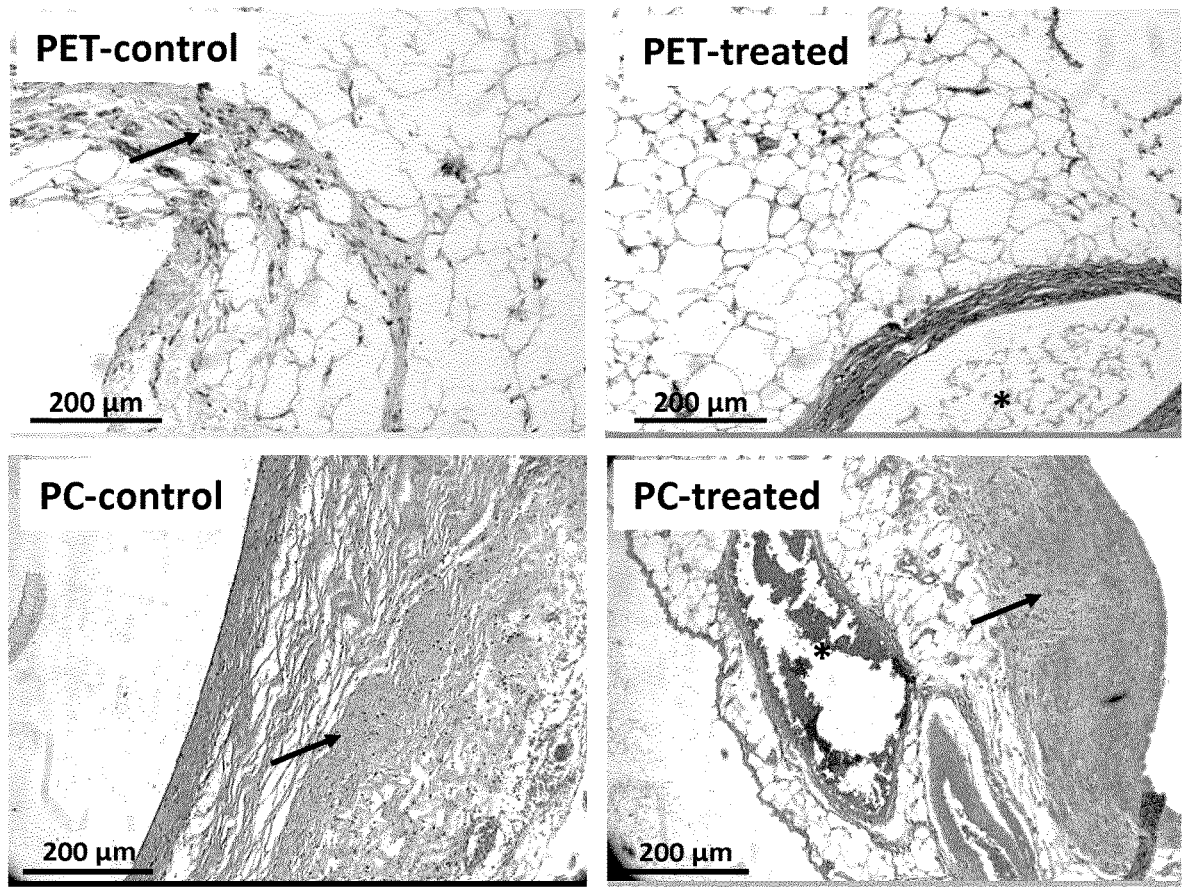
FIG. 3: Images of the sections prepared 30 days after the implantation of poly(ethylene terephthalate) (PET) or polycarbonate (PC) membranes according to the invention, treated or not treated with heparin, EC and HPMC. The surface treatment decreases fibrosis and cell infiltration (black arrows) and increases vascularization (*) for the two types of membrane.

The results are shown in FIG. 3: it is observed that the surface treatment with heparin reduces fibrosis and cell infiltration (black arrows) and increases vascularization (*) for the two types of membrane.

Example 5: Test for Glucose-Stimulation of Islets Through the Membrane a) Isolation of Rat Pancreatic Islets Animals Used The animals used are male Wistar rats weighing 250-300 g (Janvier Laboratory, Le Genes St. Ile, France). The rats are housed in standard collective cages at a temperature of 23±1° C., and a hygrometry of 55±3% and with a cycle of 12 h of light and 12 h in the dark. SAFE-A04 feed (Villemoisson-sur-Orge, France) and water are available ad libitum. The animal experiments are carried out in accordance with European directive 2010/63/EU.

Removal of the Pancreas

The animal is anaesthetized with a mixture of Imalgene 1000® (active ingredient: ketamine, Centravet ref: IMA004) supplemented with 2.7 ml of Rompun® (active ingredient: xylazin at 2%, Centravet ref: ROM001) injected intraperitoneally at a dose of 100 µl/100 g of body weight.

After having verified the absence of reflexes of the animal, the latter is laid on its back. A laparotomy is then performed and the bile duct is ligatured at its duodenal opening. It is then catheterized at its hepatic opening and the animal is sacrificed by exsanguination. 10 ml of collagenase type XI (Sigma, ref: C7657) at 1 mg/ml at 4° C. are then injected into the pancreas by means of the catheter.

The pancreas is then removed and placed in a 50 ml Falcon tube containing 3.75 ml of sterile "perfusion solution". This solution is composed of 500 ml of HBSS (Hanks Balanced Salt Solution, Lonza, ref: BE10-527F), 2.1 ml of 8.4% sodium bicarbonate, 1.175 ml of 1M calcium chloride and 12.5 ml of 1M HEPES. In order to limit the action of the enzyme during the removal, the tubes containing the pancreases are kept in ice.

Digestion

Immediately after the pancreases have been removed, the tube is placed in a waterbath at 37° C. for 10 minutes. It is then vigorously stirred for a few seconds in order for the tissue to be well dissociated. It is then made up with a cold washing solution. The washing solution is composed of M199 (Sigma, ref: M0393-50L) supplemented with 0.35 g/l of sodium bicarbonate (Sigma, ref: S-5761), with 10% of foetal calf serum (FCS, Lonza, ref: DE14-801F) and with 1% of anti-mycotic antibiotic (AMAB, Fisher, ref: W3473M).

The content of the tube is filtered on inserts (Corning Netwell inserts, Sigma, ref: CLS3480) and the filtrate is transferred into a 200 ml Corning tube which is centrifuged for 1 minute at 1200 rpm at 4° C. The supernatant is then removed and the pellet is resuspended with cold washing solution, then transferred into a 50 ml Falcon tube. After centrifugation for 1 minute at 1200 rpm at 4° C., a maximum amount of supernatant is removed before going on to the purification step.

Purification

The purification of the islets is carried out using a discontinuous gradient of Ficoll (Fisher, ref: BP525-500) which is composed of 3 solutions of different densities prepared in the laboratory: 1.108 (Ficoll 1): 1.108, 1.096 (Ficoll 2): 1.096 and 1.069 (Ficoll 3): 1.069.

The cell pellet is resuspended in 12 ml of Ficoll 1, and 10 ml of Ficoll 2 then of Ficoll 3 are carefully added on the top. Finally, 5 ml of PBS (Fisher, ref: 20012-019) are deposited on the Ficoll 3. The whole assembly is centrifuged for 4 minutes at 400 rpm at 4° C. and then for 12 minutes at 2000 rpm at 4° C. The braking and accelerating speeds of the centrifuge are adjusted to the minimum so as not to disturb the gradients.

The islets are recovered at the interface between the Ficoll 2 and the Ficoll 3, and are then washed three times in a cold washing solution in order to remove any trace of Ficoll.

Culturing

The islets are cultured in M199 medium (Gibco, ref: 23340-020) containing 10% of FCS (Lonza, ref: DE14-801F) and 1% of AMAB (Fisher, ref: W3473M) in untreated 25 cm2 flasks (Dutscher, ref: 690195), for 24 hours at 37° C. and in a humid atmosphere at 5% $CO_2$.

b) Stimulation Test

Ten rat islets are placed in inserts (type of cylinders) at one end of which the PET membrane is attached. This membrane is oriented in such a way that the nanoporous membrane (which has pores with an internal diameter between 10 and 50 nm and which is selective for molecules up to 150 kDa) is on the inside of the insert, in contact with the rat islets, the layer which has the pores with a diameter of between 400 and 600 nm being oriented towards the outside of the insert.

The insert contains 400 µl of Krebs solution containing 10% of FCS and 2.5 mM of glucose. The inserts thus filled are placed in wells of a 24-well plate containing 1 ml of Krebs solution containing 10% of FCS and 25 mM of glucose. The 24-well plate is then incubated at 37° C. and samples of medium contained in the wells are taken at 1 h, 2 h, 4 h, 6 h, 8 h and 24 h. The insulin is then assayed in the samples using the ELISA method (Mercodia, ref: 1250-01).

The islets are also sampled and placed in 50 µl of lysis buffer (ThermoScientific, ref: 78501), supplemented with a protease inhibitor (ThermoScientific, ref: 78441), in order to extract the total proteins. The extraction is carried out by placing the tubes on ice for 30 min, while regularly vortexing the samples. The total protein content of the islets is determined by means of a Bradford assay and is used to normalize the secretion of insulin between the various islet cultures.

Example 6: Implantation and Explanation of MAILPAN® in Pigs

An encapsulating chamber (MAILPAN®, for MAcro-encapsulation d'ILots PANcréatiques [macro-encapsulation of pancreatic islets]) is prepared according to the method described in WO 2012/010767. Two semi-permeable membranes are welded together. This encapsulating chamber has an internal sheet, and also connectors.

Anaesthesia

Premedication is systematic before any anesthesia and consists of the intramuscular administration of a combination of a butyrophenone: 2 mg/kg azaperone (Stresnil*) and of 10 mg/kg ketamine (Imalgene*).

General anesthesia is carried out according to the protocol described hereinafter:

the animals are taken, premedicated, to the operating block and placed on the operating table lying on their side.

A peripheral vein is catheterized (G 22) on one ear and its permeability is ensured by rinsing with a 0.9% NaCl solution.

The induction is carried out by intravenous injection of a hypnotic (5 mg/kg thiopental or 4 mg/kg propofol) and of a curarising agent (0.1 mg/kg pancuronium). It is immediately followed by orotracheal intubation (Portex Blue Line, low-pressure balloon, calibre 6 for a subject weighing 25 to 35 kg) and by pulmonary ventilation using a semi-closed circular system connected to a respirator operating in controlled pressure mode. The ventilation ($FiO_2$=0.5 $FiN_2O$=0.5) is adjusted so as to maintain $E_TCO_2$ between 35 and 45 mmHg. The respirator is a latest-generation human apparatus (GE Avance*, Aisys* or Aespire*) fitted with current flow rate, pressure and volume controls.

The anaesthesia is maintained on inhalation mode with isoflurane (fraction inspired=2 vol %) with a fresh gas flow rate of 2 l/min of a 50%/50% $O_2N_2O$ mixture serving as vector gas.

If it proves to be necessary, the administration of subsequent doses of pancuronium provides optimum muscle relaxation under coverage of deep inhalation anaesthesia (MAC of isoflurane in pure $O_2$=1.15 vol % and MAC of $N_2O$=110 vol %.

MAILPAN® Implantation

After anesthesia of the animals, the abdomen of the animals sent to sleep is made aseptic using 70% ethanol and then betadine (taking care not to cause hypothermia) and is shaved using a scalpel blade. A longitudinal incision of approximately 10 to 15 centimeters of the skin and muscle planes as far as the peritoneum is made in the middle of the cleared zone. After a median laparotomy, the prototype is implanted extraperitoneally, after being filled with physiological saline, and is attached to the wall with thread (Vicryl 2/0). The two catheters of the MAILPAN (one being used for the filling and the other for the emptying of the islets in the MAILPAN, in a period subsequent to the implantation) are connected to two injection chambers placed subcutaneously, before ligature of the peritoneum by sinusoidal movement, using 4-0 suture thread.

At the end of the surgery, the wounds are infiltrated with Naropein, and fentanyl will be administered IV before the animal is woken up. Fentanyl granules are administered per-operatively with the food intake, in a proportion of 2 mg/kg.

MAILPAN® Explanation

The MAILPAN devices are explanted 15 days and 60 days post-transplantation under general anesthesia in order to evaluate the mechanical strength of the MAILPAN, the sterility thereof and the biocompatibility thereof (vascularization at the surface, absence of inflammation, absence of fibrosis and of inflammation on the surrounding tissues). Thus, samples of tissues surrounding the MAILPAN are taken at each explanation of the device for subsequent histological tests. The pigs are sacrificed after each explanation by intravenous injection of KCl.

The tissue samples are taken under the same conditions as for the rat (see Example 5: same solutions for tissues and membranes, same analyses carried out).

Example 7: Analyses of the Membranes by Scanning Electron Microscopy

After sampling, the membranes are rinsed in ultrapure water and fixed for 24 to 48 h at 4° C. in glutaraldehyde (Sigma, ref: G5882) diluted to 2.5%. The fixed membranes are then rinsed for 10 minutes in ultrapure water.

The samples are then dehydrated using successive baths of ethanol: two baths of 10 minutes in 50% ethanol, one bath of 25 minutes in 70% ethanol, then one bath of 10 minutes in 95% ethanol and, finally, two baths of 10 minutes in 100% ethanol. In order to completely remove the traces of water which might still be present in the samples, an incubation for 2 minutes is carried out in hexamethyldisilazane (HMDS) (Sigma, ref: 440191).

After drying in the open air, the samples are then adhesively bonded flat on blocks (Delta Microscopies, ref: 75220), using carbon-conducting adhesive (Delta Microscopies, ref: 76510).

Once the adhesive has solidified, the samples are metallized by depositing a thin layer of gold-palladium, and then of carbon.

The observation is carried out on a field-effect scanning electron microscope (SEM) (Hitachi S800) (in vitro imaging platform of the Neurochemistry Centre of Strasbourg) at a voltage of 5 KV, which makes it possible to obtain good resolution without damaging the samples.

Results

Figure 4:
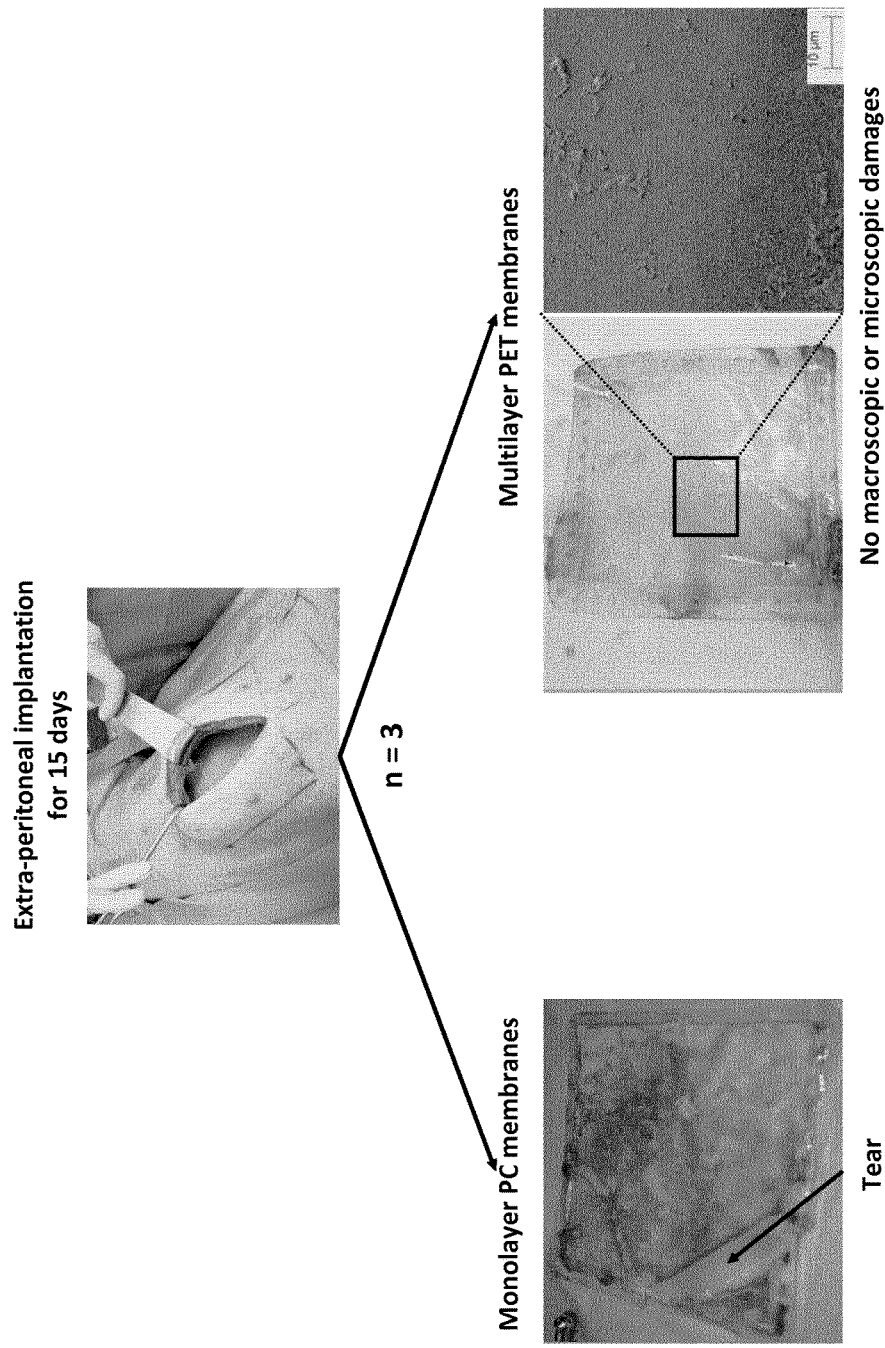
FIG. 4: Appearance of the bioartificial organs after 15 days of implantation in pigs. One of the devices is composed of monolayer PC membranes and the other of multilayer PET membranes. The device with PC membranes shows wide tears. The device with multilayer PET membranes does not, for its part, show any macroscopic damage. Said multilayer PET membranes were thus analyzed by scanning electron microscopy, which demonstrated no microcracks.

It is observed that the device produced with PC membranes shows wide tears (FIG. 4).

On the other hand, the device produced with the multi-layer PET membranes does not, for its part, show any macroscopic damage. Said membranes were thus analyzed by scanning electron microscopy, which demonstrated no microcracks (FIG. 4).

It therefore appears that the membranes according to the invention allow a diffusion similar to that observed for the prior art membranes and clearly have the property of semi-permeability (blocking IgGs, and other proteins of the immune system). These membranes exhibit much better resistance when they are used in a bioartificial organ implanted in vivo.

Further data has been obtained for tensile strength in vitro, for PET membranes. The strength is slightly higher for a tri-layer membrane (two porous PET membranes surrounding a non-woven PET membrane), than for a two-layer membrane (one porous PET membrane laminated on a non-woven PET membrane). The tensile strength of the two-layer membrane is higher than the one for a mono-layer porous PET membrane.

The invention claimed is:

1. A method for treating a patient in need thereof, comprising the step of implanting a bioartificial organ in the body of the patient, wherein the bioartificial organ comprises a chamber comprising a closed shell made of a semi-permeable membrane, delimiting a space capable of containing said secreting cells producing at least one substance of therapeutic interest, wherein said membrane comprises a layer of biocompatible non-woven polymer located between two layers of porous biocompatible polymers, wherein the chamber encapsulates secreting cells producing at least one substance of therapeutic interest for the patient.

2. The method of claim 1, wherein said membrane consists of a layer of biocompatible non-woven polymer located between two layers of porous biocompatible polymers.

3. The method of claim 1, wherein said non-woven biocompatible polymer is chosen from the group consisting of polycarbonate (PC), polyethyleneimine, polypropylene (PP), poly(ethylene terephthalate) (PET), poly(vinyl chloride) (PVC), polyamide, and polyethylene (PE).

4. The method of claim 1, wherein said porous biocompatible polymer of at least one layer is chosen from the group consisting of polycarbonate (PC), polyethyleneimine, polypropylene (PP), poly(ethylene terephthalate) (PET), poly(vinyl chloride) (PVC), polyamide, and polyethylene (PE).

5. The method of claim 1, wherein at least one, or the two layer(s) of porous biocompatible polymer is (are) made hydrophilic by surface physical or chemical modification, and covered with at least one hydrophilic polymer.

6. The method of claim 1, wherein one of the two layers of porous biocompatible polymers has a pore density of between $10^6$ pores/cm$^2$ and $10^{11}$ pores/cm$^2$.

7. The method of claim 1, wherein the total thickness of the membrane is between 45 µm and 200 µm.

8. The method of claim 1, wherein the thickness of one of the layers of biocompatible polymer is between 5 and 40 µm, and the thickness of the other layer of biocompatible polymer is between 25 and 100 µm.

9. The method of claim 1, wherein the internal diameter of the pores present on one of the layers of biocompatible polymer is between 5 and 100 nm, and the internal diameter of the pores present on the other layer of biocompatible polymer is between 100 and 2000 nm.

10. The method of claim 5, wherein at least one layer is covered with a hydrophilic polymer which contains at least one biologically active molecule.

11. The method of claim 1, further comprising a biocompatible sheet contained in said shell, said sheet optionally comprising projections at its surface.

12. The method of claim 2, wherein the layer external to the shell has pores with an internal diameter of between 100 and 2000 nm, and the layer internal to the shell has pores with an internal diameter of between 5 and 100 nm.

13. The method of claim 1, wherein the chamber comprises at least one connector which makes it possible to establish a communication between the exterior and the interior of the shell.

14. The method of claim 1, wherein the chamber is circular and has a diameter of between 3 cm and 20 cm.

15. The method of claim 1, wherein said non-woven polymer is polyester.

16. The method of claim 1, wherein said porous biocompatible polymer of at least one layer is polyester.

17. The method of claim 1, wherein the internal diameter of the pores present on one of the layers of biocompatible polymer is between 5 and 100 nm, and the internal diameter of the pores present on the other layer of biocompatible polymer is between 200 and 1000 nm.

18. The method of claim 1, wherein the patient has diabetes and the encapsulated cells secrete insulin.

19. The method of claim 1, wherein the bioartificial organ is implanted in the intraperitoneal cavity or in the extraperitoneal space.

20. The method of claim 1, wherein the bioartificial organ comprises at least one connector and a tube connected to the connector, the method further comprising filling and emptying the bioartificial organ to renew the cells.

21. The method of claim 2, wherein said non-woven biocompatible polymer is chosen from the group consisting of polycarbonate (PC), polyethyleneimine, polypropylene (PP), poly(ethylene terephthalate) (PET), poly(vinyl chloride) (PVC), polyamide, and polyethylene (PE).

22. The method of claim 2, wherein said porous biocompatible polymer of at least one layer is chosen from the group consisting of polycarbonate (PC), polyethyleneimine, polypropylene (PP), poly(ethylene terephthalate) (PET), poly(vinyl chloride) (PVC), polyamide, and polyethylene (PE).

23. The method of claim 2, wherein at least one, or the two, layer(s) of porous biocompatible polymer is (are) made hydrophilic by surface physical or chemical modification, and covered with at least one hydrophilic polymer.

24. The method of claim 2, wherein one of the two layers of porous biocompatible polymers, has a pore density of between $10^6$ pores/cm$^2$ and $10^{11}$ pores/cm$^2$.

25. The method of claim 2, wherein the total thickness of the membrane is between 45 µm and 200 µm.

26. The method of claim 2, wherein the thickness of one of the layers of biocompatible polymer is between 5 and 40 µm, and the thickness of the other layer of biocompatible polymer is between 25 and 100 µm.

27. The method of claim 2, wherein the internal diameter of the pores present on one of the layers of biocompatible polymer is between 5 and 100 nm, and the internal diameter of the pores present on the other layer of biocompatible polymer is between 100 and 2000 nm.

28. The method of claim 23, wherein at least one layer is covered with a hydrophilic polymer which contains at least one biologically active molecule.

29. The method of claim 2, wherein the chamber further comprises a biocompatible sheet contained in said shell, said sheet optionally comprising projections at its surface.

30. The method of claim 2, wherein the layer external to the shell has pores with an internal diameter of between 100 and 2000 nm, and the layer internal to the shell has pores with an internal diameter of between 5 and 100 nm.

31. The method of claim 2, wherein the chamber comprises at least one connector which makes it possible to establish a communication between the exterior and the interior of the shell.

32. The method of claim 2, wherein the chamber is circular and has a diameter of between 3 cm and 20 cm.

33. The method of claim 2, wherein said non-woven polymer is polyester.

34. The method of claim 2, wherein at least one of the layers of porous biocompatible polymer of is polyester.

35. The method of claim 2, in which the internal diameter of the pores present on one of the layers of biocompatible polymer is between 5 and 100 nm, and the internal diameter of the pores present on the other layer of biocompatible polymer is between 200 and 1000 nm.

36. The method of claim 2, wherein the patient has diabetes and the encapsulated cells secrete insulin.

37. The method of claim 2, wherein the bioartificial organ is implanted in the intraperitoneal cavity or in the extraperitoneal space.

38. The method of claim 2, wherein the bioartificial organ comprises at least one connector and a tube connected to the connector, the method further comprising filling and emptying the bioartificial organ to renew the cells.

\* \* \* \* \*